United States Patent [19]

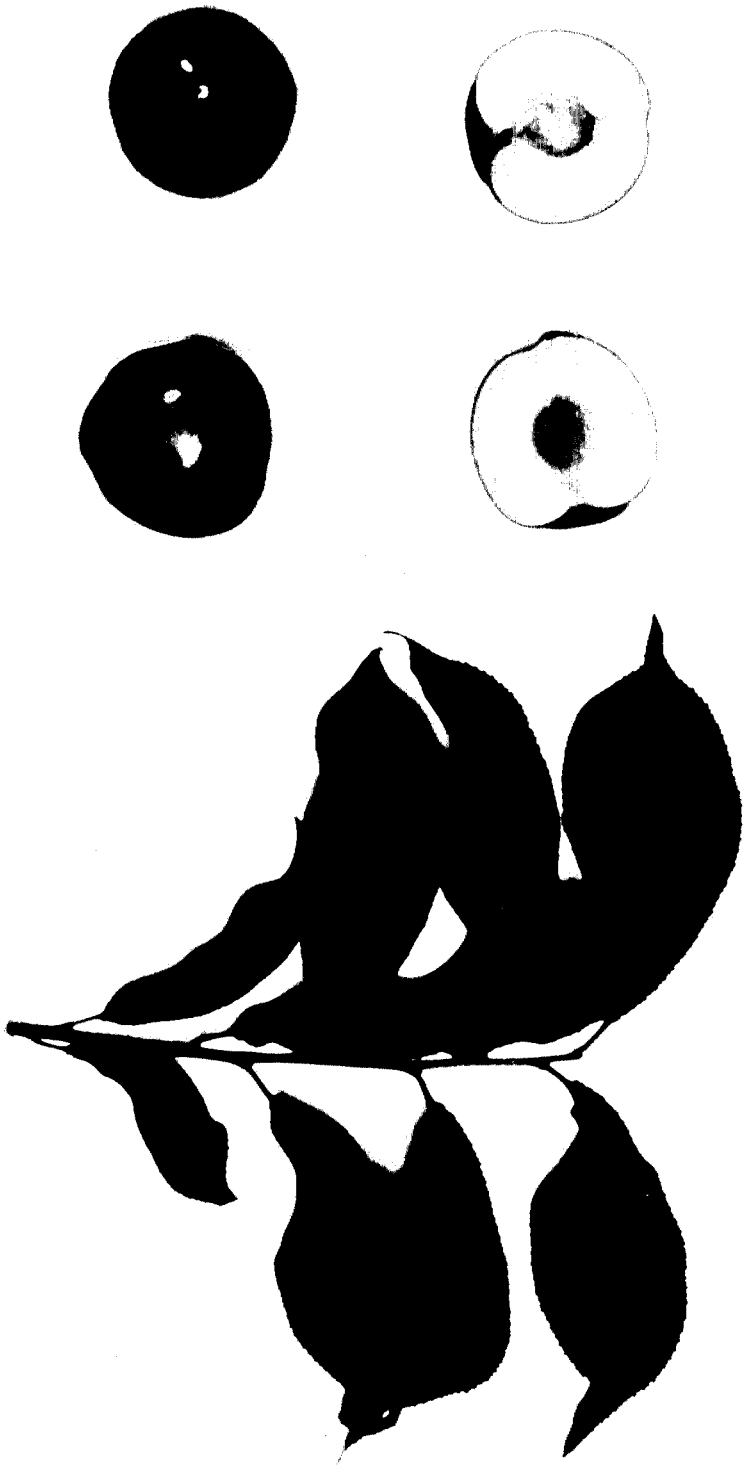

Kitahara et al.

[11] Plant 4,621

[45] Jan. 13, 1981

[54] PLUM TREE

[76] Inventors: Lawrence K. Kitahara; Kei Kitahara, both of 242 W. Palm, Reedley, Calif. 93654

[21] Appl. No.: 55,647

[22] Filed: Jul. 9, 1979

[51] Int. Cl.[3] ..... A01H 5/00

[52] U.S. Cl. ..... Plt./38

[58] Field of Search ..... Plt./38

*Primary Examiner*—Edgar S. Burr

*Assistant Examiner*—James R. Feyrer

*Attorney, Agent, or Firm*—Huebner & Worrel

[57] ABSTRACT

A plum tree generally similar to the Red Beaut Plum Tree (U.S. Plant Pat. No. 2,539) which it most nearly resembles, bearing reddish skinned, yellow-fleshed clingstone fruit which ripens from five to seven days earlier than and is larger, more highly colored, and of superior texture and flavor to that of the Red Beaut.

2 Drawing Figures

BACKGROUND OF THE VARIETY

The present invention relates to a new and distinct variety of plum tree which is generally similar to the Red Beaut Plum Tree (U.S. Plant Pat. No. 2,539) of which it is a mutation, but which bears fruit which is larger and has a richer reddish color, has a more meaty, crisper, and less fibrous texture, is sweeter and has a more delicate vinuous flavor than that of the Red Beaut variety, and is especially characterized by ripening five to seven days earlier than the fruit of the Red Beaut.

The Red Beaut Plum Tree is well known as being vigorous and as a regular productive bearer of medium sized, clingstone fruit having flesh which is yellow when picking ripe and of a delicate flavor, having a skin of a generally red, maroon, or purple hue, and having good shipping and keeping qualities. The Red Beaut Plum is particularly desirable for the very early ripening of its fruit.

As with all produce, the time of harvest of plums greatly influences the prices the plums bring in the market, fruit which can be marketed early usually commanding a higher price. However, in many cases fruit of an early ripening variety is inferior in size, color, or eating quality to that of later ripening varieties with the result that such fruit cannot be marketed at a higher price than that of superior quality, later ripening fruit. It has long been recognized as desirable to provide a plum tree which bears fruit ripening even earlier than that of the early ripening Red Beaut variety without sacrificing any of the desirable qualities of the fruit of said variety. It is, of course, even more desirable to provide such an extremely early bearing new plum tree whose size, color, and eating qualities are superior to those of the Red Beaut.

ORIGIN AND ASEXUAL REPRODUCTION OF THE NEW VARIETY

The new variety of plum tree was discovered by us in May, 1977 as a bud mutation growing in an orchard of Red Beaut Plum Trees (U.S. Plant Pat. No. 2,539) located on the northeast corner of McKinley and Del Rey Avenues near the City of Fresno, in the County of Fresno, in the State of California. Said orchard is a portion of a ranch owned by Lawrence K. Kitahara, Susan Ruth Kitahara, and Kitahara Farms, Inc., a corporation of California.

The mutation was asexually reproduced by us by budding in June, 1977 into Red Rosa (unpatented) plum trees located on said ranch and the fruit and the characteristics resulting from such budding provided identical to those of the original mutation.

SUMMARY OF THE NEW VARIETY

The instant variety of plum tree is characterized by perpetuating the general characteristics of the Red Beaut Plum Tree, but has the important distinction of ripening from five to seven days earlies under the growing conditions prevailing in the San Joaquin Valley of California. The fruit of the new variety was picked ripe on May 21st in 1977 and on May 24th in 1978. When grown in the same environment and under the same cultural practices, fruit borne by the new variety, in comparison with that of the Red Beaut, also is of larger size, is more globose, has a more richly colored skin, and has flesh of a more tender and less fibrous texture and yet crisper and more meaty. The fruit of the new variety is of a superior delicate and vinuous flavor as compared to that of the Red Beaut variety. The new variety is further distinguished from the Red Beaut in that the kernels of the new variety are more bitter in taste and are more likely to be viable. The bark of the two year old wood of the new variety is less grayish in color than that of the Red Beaut variety, and its leaves are rougher in texture with more reddish mid veins and petioles than the leaves of the Red Beaut variety. The fruit of the new variety is clingstone, of medium size and globose and uniform form and has a skin which is uniformly colored from Maroon (7-L-7) to Saraband (6-K-8) when picking ripe and has flesh which is Popcorn Yellow (9-K-3) in color. When eating ripe, the skin of the fruit of the new variety is from Burgundy Red to Blackish Maroon in color.

BRIEF DESCRIPTION OF THE DRAWING

The accompanying drawing is a color photograph of mature plums of the subject variety with two of the plums divided to show the flesh color, together with a typical twig showing characteristic leaves.

DETAILED DESCRIPTION

Referring more specifically to the pomological details of this new and distinct variety of plum tree, the following has been observed under the ecological conditions prevailing at the designated orchard in Fresno County, Calif. All of the color code plate indications are by reference to the Maerz and Paul Dictionary of Color except where common terms of color definition are employed.

TREE

Size: Large, hardy, medium vigor.

Figure: Spreading, open, vase shaped, when properly pruned.

Productivity: Productive, regular bearing.

Trunk: Thickness — medium; texture of bark — medium.

Branches:

*Thickness.*—Medium.

*Texture of bark.*—Medium, smooth on two to three year old wood.

*Color.*—Green branches — glossy, Olive Wood (15-E-10). Current season's growth — dorsal side, Old Rose Leaf (7-J-3); ventral side, Sea Green (19-K-6). One year old wood — light brown with grayish overcolor. Two to three year old wood — less grayish than Red Beaut variety; dorsal side, gray; ventral side, light brown flecked with gray. Older fruiting limbs — dorsal side, dusty gray; ventral side, Collie (22-A-1). Lenticels — number, medium; size, small but larger on older wood; very small on current seaons's growth with more on dorsal side; small and few on one year old wood.

Leaves:

*Size.*—Medium; average length 98 mm, average width 48 mm, medium thickness.

*Form.*—Oblanceoate to obovate; tip, accuminate; base, mostly acute; margin, doubly crenate.

*Texture.*—Rugose, more so than the Red Beaut variety.

*Veins.*—Pinnately net veined.

*Color.*—Dorsal side, Vernon Green (23-L-8); ventral side, Cress Green (22-I-6).

*Petioles.*—Medium length and thickness; dorsal side color Haematite Red (7-H-2) to Moss Green (21-L-2); ventral side color Calabash Medal Bronze (14-J-7) to Wineberry (55-J-4).

*Glands.*—Average number two; disposed at base of leaf blade, mostly oppositely; reniform; medium to small in size with a few large; mostly green in color with a few red.

*Stipules.*—Present on approximately fifteen percent of current season's growth at leaf nodes, 6 to 7 mm in length.

*Leaf buds.*—Small, roundish pointed.

Flower buds: Hardy; small, glabrous; free; short; and plump.

Flowers: Small; white; early blooming, in 1979 first bloom was February 24 and full bloom was March 5.

Pollenization: Set fruit in 1979 when pollenized by bouquets of flowers from the Santa Rosa (unpatented), El Dorado (unpatented), and Wickson (unpatented) varieties of plum trees.

FRUIT

Maturity: Five to seven days before Red Beaut.

*Picking ripe.*—May 21, 1977; May 24, 1978.

*Eating ripe.*—June 3, 1978.

Size: Mostly uniform, mostly large, some medium; axial diameter — 41.4 mm average; transverse diameter in suture plane — 41.2 mm average.

Form: Mostly uniform, globose to round — ovate; longitudinal section — round, slight ovate; transverse section through diameter — round.

*Suture.*—Inconspicuous shallow line; extends from base to beyond apex but is discontinuous thereat; slight depression beyond pistil point.

*Ventral surface.*—Slightly rounded, lipped base to apex, lips mostly equal.

*Cavity.*—Flaring, elongated in suture plane with suture showing on both sides, medium broad, shallow; depth — 8.8 mm average; width — 13 mm average; length — 18+ mm average.

*Base.*—Some cuneate, many truncate with slight projection on ventral side.

*Apex.*—Short, rounded, apical.

*Stem.*—Medium, length — 15 mm average, width — 2 mm average, color — Russet Green (20-K-1).

Skin: Thin; medium texture; slightly astringent; tenacious to flesh; no tendency to crack; glabrous.

*Color.*—Picking ripe — uniform over entire fruit from Maroon (7-L-7) to Saraband (6-K-8); eating ripe — Burgundy Red to Blackish Maroon; bloom — heavy, light blueish.

Flesh:

*Color.*—Popcorn Yellow (9-K-3) including surface of pit cavity.

*Amygdalin.*—Wanting.

*Juice.*—Moderate quantity, rich.

*Texture.*—Mostly firm, crisp, meaty, melting.

*Fibers.*—Few, fine, tender.

*Ripening.*—Fairly even; earliest at apex, suture, and along both lips.

*Flavor.*—Sweet to mild, delicate, vinuous.

*Aroma.*—Wanting.

*Eating quality.*—Very good.

Stone: Cling; adheres to flesh over entire surface on longitudinal section, adherence varies with ripeness; short fibers; no tendency to split.

*Size.*—Mostly medium, a few large; length — 18 mm average; breadth — 17.7 mm average; thickness — 8.5 mm average.

*Form.*—Mostly globose; cuneate toward base; base mostly straight, many cupped; hilum mostly narrow.

*Apex.*—Wide, rounded with short oceate tip, curved on both sides.

*Surface.*—Regularly furrowed near base and toward apex on ventral side; pitted mostly on sides, pits irregular in shape; ridges rounded and mostly toward base.

*Ventral edge.*—Thin, with wing toward base.

*Dorsal edge.*—Narrow, thicker than ventral edge.

*Edge ridges.*—Present on both sides, interrupted.

*Color.*—Golden Wheat (11-E-7).

*Wall thickness.*—Medium.

*Kernel.*—Form — ovate. Taste — slightly bitter. Amygdalin — moderate. Pellicle color — Gold Leaf (11-K-8). Width — 8 mm average. Length — 9 mm average. Viability — 15 to 30 percent.

Use: Dessert, cullinary.

*Keeping quality.*—Good.

*Shipping quality.*—Good.

*Resistance to insects.*—Apparently good.

*Resistance to disease.*—Apparently good.

Although the new variety of plum tree bears the described characteristics as a result of the growing conditions in Fresno County, Calif., in the central part of the San Joaquin Valley, it is to be understood that variations of the usual magnitude in characteristics incident to growing conditions, fertilization, pruning, and pest control are to be expected.

Having thus described and illustrated our new variety of plum tree, what is new and desired to be secured by Letters Patent is:

1. A new and distinct variety of plum tree, substantially as illustrated and described, characterized by its regular and productive bearing of clingstone fruit of medium size having a reddish skin and flesh which is yellow when the fruit is picking ripe and by its resemblance to the Red Beaut Plum Tree (U.S. Plant Pat. No. 2,539) but from which it is distinguished by bearing fruit ripening from five to seven days earlier, having flesh of a more tender and less fibrous texture and a more delicate vinuous flavor, and having a more globose shape and a more highly colored skin.

* * * * *

UNITED STATES PATENT AND TRADEMARK OFFICE

CERTIFICATE OF CORRECTION

PATENT NO. : Plant 4621
DATED : January 13, 1981
INVENTOR(S) : Lawrence K. Kitahara & Kei Kitahara It is certified that error appears in the above-identified patent and that said Letters Patent are hereby corrected as shown below:

Column 2, line 2, delete "provided" and substitute ---proved---.

Signed and Sealed this

*Twenty-first* Day of *April 1981*

[SEAL]

*Attest:*

RENE D. TEGTMEYER

*Attesting Officer* *Acting Commissioner of Patents and Trademarks*